US012571059B2

(12) United States Patent (10) Patent No.: US 12,571,059 B2
Hamilton et al. (45) Date of Patent: Mar. 10, 2026

(54) COMPOSITIONS AND METHODS FOR DETECTION OF EPSTEIN BARR VIRUS (EBV)

(71) Applicant: Roche Molecular Systems, Inc., Pleasanton, CA (US)

(72) Inventors: Aaron T. Hamilton, Mountain House, CA (US); Marintha Heil, Danville, CA (US); Debra Liggett, Pleasanton, CA (US); Jingtao Sun, San Ramon, CA (US); Ling Wang, Dublin, CA (US); Xiaoning Wu, Fremont, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 1087 days.

(21) Appl. No.: 17/597,725

(22) PCT Filed: Jul. 24, 2020

(86) PCT No.: PCT/EP2020/070896
§ 371 (c)(1),
(2) Date: Jan. 20, 2022

(87) PCT Pub. No.: WO2021/013972
PCT Pub. Date: Jan. 28, 2021

(65) Prior Publication Data
US 2022/0251670 A1 Aug. 11, 2022

Related U.S. Application Data

(60) Provisional application No. 62/878,643, filed on Jul. 25, 2019.

(51) Int. Cl.
*C12Q 1/6813* (2018.01)
*C12Q 1/6844* (2018.01)
*C12Q 1/70* (2006.01)

(52) U.S. Cl.
CPC ............. *C12Q 1/70* (2013.01); *C12Q 1/6813* (2013.01); *C12Q 1/6844* (2013.01)

(58) Field of Classification Search
None
See application file for complete search history.

(56) References Cited

U.S. PATENT DOCUMENTS

2016/0251724 A1 9/2016 Ng

FOREIGN PATENT DOCUMENTS

| CN | 107354239 A | 11/2017 |
| JP | 2004536282 A | 12/2004 |
| JP | 2012090633 A | 5/2012 |

OTHER PUBLICATIONS

Jordan et al., "Advanced diagnostic methods in oral and maxillofacial pathology. Part I: Molecular methods", Oral Surgery Oral Medicine Oral Patholology, December, vol. 92, No. 6, pp. 650-669. (Year: 2001).*
Shao et al., "Comparison of Epstein-Barr Virus DNA Level in Plasma, Peripheral Blood Cell and Tumor Tissue in Nasopharyngeal Carcinoma," Anticancer Research, vol. 24, pp. 4059-4066. (Year: 2004).*
Google-English Translation of CN107354239A [retrieved on-line, retrieval date: May 22, 2025; retrieved from: https://patents.google.com/patent/CN107354239A/en?oq=cn107354239] (Year: 2025).*
Ambinder, R.F., et al., Oligonucleotides for polymerase chain reaction amplification and hybridization detection of Epstein-Barr virus DNA in clinical specimens, Molecular and Cellular Probes, Oct. 1, 1990, pp. 397-407, vol. 4, No. 5.
Guo, C., et al., Prevalence and characteristics of Epstein-Barr virus associated gastric carcinoma in Gansu Province, Northwest China with mRNA expression of glycoprotein BMRF2, Journal of Medical Virology, Oct. 30, 2019, pp. 356-363, vol. 92, No. 3.
International Search Report issued Oct. 13, 2020 in Application No. PCT/EP2020/070896, 19 pages.
Jordan, R.C.K., et al., Advanced diagnostic methods in oral and maxillofacial pathology. Part I: Molecular methods, Oral Surgery, Oral Medicine, Oral Pathology, Oral Radiology and Endodontics, Dec. 2001, pp. 650-669, vol. 92, No. 6.
Kimura, et al., Measuring Epstein-Barr virus (EBV) Load: the significance and application for each EBV-associated Disease, Reviews in Medical Virology, 2008_vol. 18_pp. 305-319.
Yen, C.-Y., et al., Detection of EBV Infection and Gene Expression in Oral Cancer from Patients in Taiwan byMicroarray Analysis, Journal of Biomedicine and Biotechnology, Jan. 1, 2009, pp. 1-15, vol. 2009, Article ID 904589.
Borozan, I., et al., Analysis of Epstein-Barr Virus Genomes and Expression Profiles in Gastric Adenocarcinoma, Journal of Virology, Jan. 2018, e01239-17, pp. 1-18, vol. 92, Issue 2.
Incomserb, P., et al., Establishment of Real-Time Polymerase Chain Reaction-Based Assay for Quantitation of Epstein-Barr Virus DNA in Healthy Donors and in Patients with EBV Associated Lymphoma, J Med Assoc Thai, 2005, pp. S280-S286, vol. 8, Suppl. 4.

* cited by examiner

*Primary Examiner* — Young J Kim
(74) *Attorney, Agent, or Firm* — Eric Grant Lee

(57) ABSTRACT

Methods for the rapid detection of the presence or absence of Epstein Barr Virus (EBV) in a biological or non-biological sample are described. The methods can include performing an amplifying step, a hybridizing step, and a detecting step. Furthermore, primers and probes targeting EBV, and kits are provided that are designed for the detection of target regions of EBV. Also described are kits, reaction mixtures, and oligonucleotides (e.g., primer and probe) for the amplification and detection of EBV. Also described are primers and probes that detect different regions of EBV, and can be employed in a dual target assay for simultaneously detecting two different and non-overlapping target regions of EBV.

15 Claims, 21 Drawing Sheets

Specification includes a Sequence Listing.

SEQ ID NO:4

SEQ ID NO:5

SEQ ID NO:6

FIG. 2

SEQ ID NO:1

SEQ ID NO:2

SEQ ID NO:3

1E3 IU/mL (plasmid)

1E4 IU/mL (supernatant)

40 IU/mL

20 IU/mL

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Forward Primer
<220> FEATURE:
<221> NAME/KEY: modified_base
<222> LOCATION: (24)..(24)
<223> OTHER INFORMATION: t-Butyl Benzyl-dC

<400> SEQUENCE: 1
catctgttgt ggtatatttc ctcc                                         24

<210> SEQ ID NO 2
<211> LENGTH: 32
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (0)..(1)
<223> OTHER INFORMATION: FAM-Thr
```

-continued

```
<220> FEATURE:
<221> NAME/KEY: misc_feature
<222> LOCATION: (6)..(7)
<223> OTHER INFORMATION: BHQ-2
<220> FEATURE:
<221> NAME/KEY: misc_feature
<222> LOCATION: (32)..(33)
<223> OTHER INFORMATION: Phosphate

<400> SEQUENCE: 2
ctgggcaaga ccgtgctgtt tatctcaatc tt                                      32

<210> SEQ ID NO 3
<211> LENGTH: 19
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (19)..(19)
<223> OTHER INFORMATION: t-Butyl Benzyl-dA

<400> SEQUENCE: 3
cgctaccccg ctaaagtaa                                                     19

<210> SEQ ID NO 4
<211> LENGTH: 21
<212> TYPE: DNA
<213> ORGANISM: Artificial Sequence
<220> FEATURE:
<223> OTHER INFORMATION: Forward Primer
<220> FEATURE:
<221> NAME/KEY: modified_base
<222> LOCATION: (21)..(21)
<223> OTHER INFORMATION: t-Butyl Benzyl-dC

<400> SEQUENCE: 4
gcgttggaaa acattagcga c                                                  21

<210> SEQ ID NO 5
<211> LENGTH: 30
<212> TYPE: DNA
<213> ORGANISM: Artificial Sequence
<220> FEATURE:
<223> OTHER INFORMATION: Probe
<220> FEATURE:
<221> NAME/KEY: misc_feature
<222> LOCATION: (0)..(1)
<223> OTHER INFORMATION: FAM-Thr
<220> FEATURE:
<221> NAME/KEY: misc_feature
<222> LOCATION: (6)..(7)
<223> OTHER INFORMATION: BHQ-2
<220> FEATURE:
<221> NAME/KEY: misc_feature
<222> LOCATION: (30)..(31)
<223> OTHER INFORMATION: Phosphate

<400> SEQUENCE: 5
ttacctggtg agcaatcaga catgcgacgg                                         30

<210> SEQ ID NO 6
<211> LENGTH: 22
<212> TYPE: DNA
<213> ORGANISM: Artificial Sequence
<220> FEATURE:
<223> OTHER INFORMATION: Reverse Primer
<220> FEATURE:
<221> NAME/KEY: modified_base
<222> LOCATION: (22)..(22)
```

-continued

<223> OTHER INFORMATION: t-Butyl Benzyl-dA

<400> SEQUENCE: 6
gttgctccca ttcttaggtg aa                                                          22

COMPOSITIONS AND METHODS FOR DETECTION OF EPSTEIN BARR VIRUS (EBV)

CROSS REFERENCE TO RELATED PATENT APPLICATIONS

This patent application is a U.S. national stage application of International Patent Application No. PCT/EP2020/070896, filed Jul. 24, 2020, which claims priority from U.S. Provisional Patent Application No. 62/878,643, filed Jul. 25, 2019, both of which are incorporated herein by reference in their entireties.

SEQUENCE LISTING

The instant application contains a Sequence Listing which has been submitted electronically in ASCII format and is hereby incorporated by reference in its entirety. The ASCII copy, created on Jul. 24, 2019, is named "35233-WO_Sequence_Listing" and is 3,000 bytes in size.

FIELD OF THE INVENTION

The present disclosure relates to the field of in vitro diagnostics. Within this field, the present invention concerns the amplification and detection of a target nucleic acid that may be present in a sample and particularly, the amplification, detection, and/or quantitation of a target nucleic acid comprising sequence variations and/or individual mutations of Epstein Barr Virus (EBV), using primers and probes. The invention further provides reaction mixtures and kits containing primers and probes for amplification and detection of EBV.

BACKGROUND OF THE INVENTION

Epstein Barr Virus (EBV) is a DNA virus, a member of the herpesvirus group (it has an alternate designation of Human Herpesvirus-4 or HHV-4). EBV infection is common, with an estimated 90% prevalence in adults, and is often asymptomatic. EBV infection can cause mononucleosis in its initial lytic stage, before entering one or more of several latent stages. EBV is highly linked with life threatening diseases in immunocompromised patients and several forms of cancer (including Burkitt's Lymphoma (BL), Hodgkin's Lymphoma (HL), Nasal NK/T-cell Lymphoma (NKTL), Lymphoepithelioma-Like Carcinoma (LELC), Nasopharyngeal Carcinoma (NPC), and Gastric Carcinoma (GC)). Immunosuppressed transplant patients are at particular risk as serious complications can arise from uncontrolled growth of latently EBV-infected B-cells leading to post-transplant lymphoproliferative disorder (PTLD). Transplantation involves a balance between rejection risk and disease risk due to immunosuppression. EBV is one of several common (90%), often asymptomatic viral infections, but which poses a threat in immunosuppressed patients, as the virus cannot be eliminated. PTLD is a proliferation of B-lymphocytes, predominantly associated with positive EBV (especially if early onset). In fact, EBV is the second major post-transplant surveillance marker (after Cytomegalovirus (CMV)), and EBV-associated PTLD is one of the most common malignancies following solid organ or hematopoietic stem cell transplantation. Up to 5% of transplant patients develop PTLD, which in the worst case can give rise to lymphoma. The highest risk group includes patients in their first year after transplant, EBV-negative recipients of EBV-positive donor organs, stem cell transplant patients, and pediatric patients. EBV can potentially be detected in the blood stream from viral particles and fragmented DNA in plasma, and also intracellular episomal DNA viral genomes and mRNA. EBV has a genome size ~172 kb or larger (depending on internal repeat number and deletions), and can exist in either linear or circular (episomal) structures. EBV genetic diversity is generally reported to include two types listed in the literature, however the actual diversity characterization of the virus is more complex and can depend on which section of the genome is sampled. EBNA2 and EBNA3A, B, and C gene sequences drive the classification of EBV strains into the traditional "type 1" and "type 2" categories. In general, type 1 is more common in most areas, although both type 1 and type 2 are highly prevalent in Africa. Outside of these genes, the type 1/type 2 divergence is less relevant and for selected genes there can be different phylogenetic patterns. Geographic variation has been described from the differences between East Asian strains of EBV and those from Europe and Africa, however sampling of more than one gene region may be needed for a full characterization of EBV genome diversity. Recombination appears to be frequent in the history of the virus, indicating reinfection or co-infection of single cells can occur. There remains a need in the art for a reliable, sensitive, and reproducible means for detecting EBV.

EBV viral load measurement is becoming a routine test for managing transplant recipients as well as diagnosing and following EBV-associated diseases. In patients undergoing monitoring of EBV virus, serial DNA measurements can be used to indicate the need for potential treatment changes and to assess viral response to treatment. Given the widespread prevalence of EBV infections in the world and the frequent recombination that occurs in EBV, there is a need in the art for a quick, reliable, specific, and sensitive method for detecting and/or quantifying the presence of EBV in a sample.

SUMMARY OF THE INVENTION

In the field of molecular diagnostics, the amplification and detection of nucleic acids is of considerable significance. Such methods can be employed to detect any number of microorganisms, such as viruses and bacteria. The most prominent and widely-used amplification technique is the Polymerase Chain Reaction (PCR). Other amplification techniques include Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification. Automated systems for PCR-based analysis often make use of a real-time detection of product amplification during the PCR process in the same reaction vessel. Key to such methods is the use of modified oligonucleotides carrying reporter groups or labels. The present invention is directed to the reliable, sensitive, and reproducible amplification and detection of EBV. Although EBV is a DNA virus with multiple well-conserved target regions for assay design, the possibility of un-encountered substitutions or deletions meant that a dual-target approach was prudent and sensible. The design of the primers and probes used available public sequence information to maximize inclusivity for EBV and exclude other herpesviruses. This invention consists of novel oligonucleotide designs, designed to maximize inclusivity of EBV and prevent cross reactivity with other templates. This EBV assay may be used on the cobas® 6800/8800. The primers and probes of the present invention may be used as a dual target assay, with both targets using the same dye, to safeguard against viral sequence heterogeneity. The design strategy was to select conserved sequence regions from the EBV genome and assess several primer and probe combinations for each target. The five regions from which assay designs were selected were the IR-1 repeat, LMP2A, EBNA-1 (BKRF-1), BMRF-2, and Reductase/BORF-2. Sequences included both type 1 and type 2 EBV, and sequences from worldwide geographic locations including Asia, Africa, North America, South America, Europe and Australia. After a screening and optimization process, the two candidates were from just beyond the final exon of EBNA-1 and from within the coding sequence of BMRF-2, were identified. These candidates could be used individually or together duplexed in a dual target assay. If used as a dual target assay, two sets of primers and probe are employed (each set detecting either EBNA-1 or BMRF-2).

Certain embodiments in the present disclosure relate to methods for the rapid detection of the presence or absence of EBV in a biological or non-biological sample, for example, multiplex detection and quantitating of EBV by real-time polymerase chain reaction (PCR) in a single test tube or vessel. Embodiments include methods of detection of EBV comprising performing at least one cycling step, which may include an amplifying step and a hybridizing step. Furthermore, embodiments include primers, probes, and kits that are designed for the detection of EBV in a single tube or vessel.

One aspect of the invention is directed to a method for detecting one or more target nucleic acids of Epstein Barr Virus (EBV) in a sample, the method comprising: (a) providing a sample; (b) performing an amplification step comprising contacting the sample with one or more set of primers to produce an amplification product, if the one or more target nucleic acids of EBV is present in the sample; (c) performing a hybridization step, comprising contacting the amplification product, if the one or more target nucleic acids of EBV is present in the sample, with one or more probes; and (d) performing a detection step, comprising detecting the presence or absence of the amplification product, wherein the presence of the amplification product is indicative of the presence of the one or more target nucleic acids of EBV in the sample, and wherein the absence of the amplification product is indicative of the absence of the one or more target nucleic acids of EBV in the sample; and wherein the one or more set of primers and the one or more probes comprise: (i) a set of primers comprising a nucleic acid sequence of SEQ ID NOs:1 and 3, or complements thereof, and a probe comprising a nucleic acid sequence of SEQ ID NO:2, or a complement thereof; and/or (ii) a set of primers comprising a nucleic acid sequence of SEQ ID NOs:4 and 6, or complements thereof, and a probe comprising a nucleic acid sequence of SEQ ID NO:3, or a complement thereof. In a related embodiment, the sample is a biological sample. In a related embodiment, the biological sample is plasma. In a related embodiment, the biological sample is blood. In another embodiment, the method is for detecting a first target nucleic acid of EBV and a second target nucleic acid of EBV in a sample, wherein the one or more set of primers and the one or more probes for detecting the first target nucleic acids of EBV comprises: (i) a set of primers comprising a nucleic acid sequence of SEQ ID NOs:1 and 3, or complements thereof, and a probe comprising a nucleic acid sequence of SEQ ID NO:2, or a complement thereof; and wherein the one or more set of primers and the one or more probes for detecting the second target nucleic acids of EBV comprises: (ii) a set of primers comprising a nucleic acid sequence of SEQ ID NO:4 and 6, or complements thereof, and a probe comprising a nucleic acid sequence of SEQ ID NO:3, or a complement thereof. In another embodiment, the first target nucleic acid of EBV and the second target nucleic acid of EBV are different. In another embodiment, the first target nucleic acid of EBV and the second target nucleic acid of EBV are not overlapping. Another aspect is directed to a method for detecting a first target nucleic acid of EBV and a second target nucleic acid of EBV in a sample, the method comprising: (a) providing a sample; (b) performing an amplification step comprising contacting the sample with two sets of primers to produce an amplification product, if the one or more target nucleic acids of EBV is present in the sample; (c) performing a hybridization step, comprising contacting the amplification product, if the one or more target nucleic acids of EBV is present in the sample, with two probes; and (d) performing a detection step, comprising detecting the presence or absence of the amplification product, wherein the presence of the amplification product is indicative of the presence of the one or more target nucleic acids of EBV in the sample, and wherein the absence of the amplification product is indicative of the absence of the one or more target nucleic acids of EBV in the sample; and wherein the one or more set of primers and the one or more probes for detecting the first target nucleic acid of EBV comprise: (i) a set of primers comprising a nucleic acid sequence of SEQ ID NOs:1 and 3, or complements thereof, and a probe comprising a nucleic acid sequence of SEQ ID NO:2, or a complement thereof; and wherein the one or more set of primers and the one or more probes for detecting the second target nucleic acid of EBV comprise: (ii) a set of primers comprising a nucleic acid sequence of SEQ ID NO:4 and 6, or complements thereof, and a probe comprising a nucleic acid sequence of SEQ ID NO:3, or a complement thereof. In another embodiment, the first target nucleic acid of EBV and the second target nucleic acid of EBV are different. In another embodiment, the first target nucleic acid of EBV and the second target nucleic acid of EBV are not overlapping. In another embodiment, the sample is a biological sample. In another embodiment, the biological sample is plasma. In another embodiment, the biological sample is blood.

Another aspect of the invention is directed to a kit for detecting one or more target nucleic acids of EBV that may be present in a sample, the kit comprising amplification reagents comprising: (a) a DNA polymerase; (b) nucleotide monomers; (c) one or more set of primers; and (d) one or more probes, wherein the one or more set of primers and the one or more probes comprise: (i) a set of primers comprising a nucleic acid sequence of SEQ ID NOs:1 and 3, or complements thereof, and a probe comprising a nucleic acid sequence of SEQ ID NO:2, or a complement thereof; and/or (ii) a set of primers comprising a nucleic acid sequence of SEQ ID NO:4 and 6, or complements thereof, and a probe comprising a nucleic acid sequence of SEQ ID NO:3, or a complement thereof. In another embodiment, the one or more probes is labeled with a donor fluorescent moiety and a corresponding acceptor moiety. In another embodiment, the kit is for detecting a first target nucleic acid of EBV and a second target nucleic acid of EBV in a sample, wherein the one or more set of primers and the one or more probes for detecting the first target nucleic acids of EBV comprises: (i) a set of primers comprising a nucleic acid sequence of SEQ ID NOs:1 and 3, or complements thereof, and a probe comprising a nucleic acid sequence of SEQ ID NO:2, or a complement thereof; and wherein the one or more set of primers and the one or more probes for detecting the second target nucleic acids of EBV comprises: (ii) a set of primers comprising a nucleic acid sequence of SEQ ID NO:4 and 6, or complements thereof, and a probe comprising a nucleic acid sequence of SEQ ID NO:3, or a complement thereof. In another embodiment, the first target nucleic acid of EBV and the second target nucleic acid of EBV are different. In another embodiment, the first target nucleic acid of EBV and the second target nucleic acid of EBV are not overlapping.

Another aspect of the invention is directed to a kit for detecting a first target nucleic acid of EBV and a second target nucleic acid of EBV in a sample, the kit comprising amplification reagents comprising: (a) a DNA polymerase; (b) nucleotide monomers; (c) a first set of primers and one probe for detecting a first target nucleic acid of EBV; and (d) a second set of primers and one probe for detecting a second target nucleic acid of EBV, wherein one first set of primers and one probe for detecting a first target nucleic acids of EBV comprises: (i) a set of primers comprising a nucleic acid sequence of SEQ ID NOs:1 and 3, or complements thereof, and a probe comprising a nucleic acid sequence of SEQ ID NO:2, or a complement thereof; and wherein the second set of primers and one probe for detecting a second target nucleic acids of EBV comprises: (ii) a set of primers comprising a nucleic acid sequence of SEQ ID NO:4 and 6, or complements thereof, and a probe comprising a nucleic acid sequence of SEQ ID NO:3, or a complement thereof. In another embodiment, the probes are labeled with a donor fluorescent moiety and a corresponding acceptor moiety. In another embodiment, the first target nucleic acid of EBV and the second target nucleic acid of EBV are different. In another embodiment, the first target nucleic acid of EBV and the second target nucleic acid of EBV are not overlapping.

Other aspects provide an oligonucleotide comprising or consisting of a sequence of nucleotides selected from SEQ ID NOs:1-6, or a complement thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs:1-6 , or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 7 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

The present disclosure also provides for methods of detecting the presence or absence of EBV or EBV nucleic acid, in a biological sample from an individual. These methods can be employed to detect the presence or absence of EBV nucleic acid in plasma, for example, for use in blood screening and diagnostic testing. Additionally, the same test may be used by someone experienced in the art to assess urine and other sample types to detect and/or quantitate EBV nucleic acid. Such methods generally include performing at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of EBV nucleic acid in the sample, and wherein the absence of binding is indicative of the absence of EBV nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of EBV nucleic acid.

In a further embodiment, a kit for detecting and/or quantitating one or more nucleic acids of EBV is provided. The kit can include one or more sets of primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of EBV nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 1 shows the EBV genome structure. FIG. 1 highlights the EBV targets BMRF2 and EBNA1, which may be used as a dual target assay.

FIG. 2 shows the EBV targets and oligonucleotide set for EBNA1, including the 96 base pair amplicon generated by the primers, and detected by the probe. FIG. 2 depicts that the forward primer has a sequence of SEQ ID NO:4, the reverse primer has a sequence of SEQ ID NO:6, and the probe has a sequence of SEQ ID NO:5.

FIG. 3 shows the EBV targets and oligonucleotide set for BMRF2, including the 98 base pair amplicon generated by the primers, and detected by the probe. FIG. 3 depicts that the forward primer has a sequence of SEQ ID NO: 1, the reverse primer has a sequence of SEQ ID NO:3, and the probe has a sequence of SEQ ID NO:2.

DETAILED DESCRIPTION OF THE INVENTION

Figures 1A, 1B:
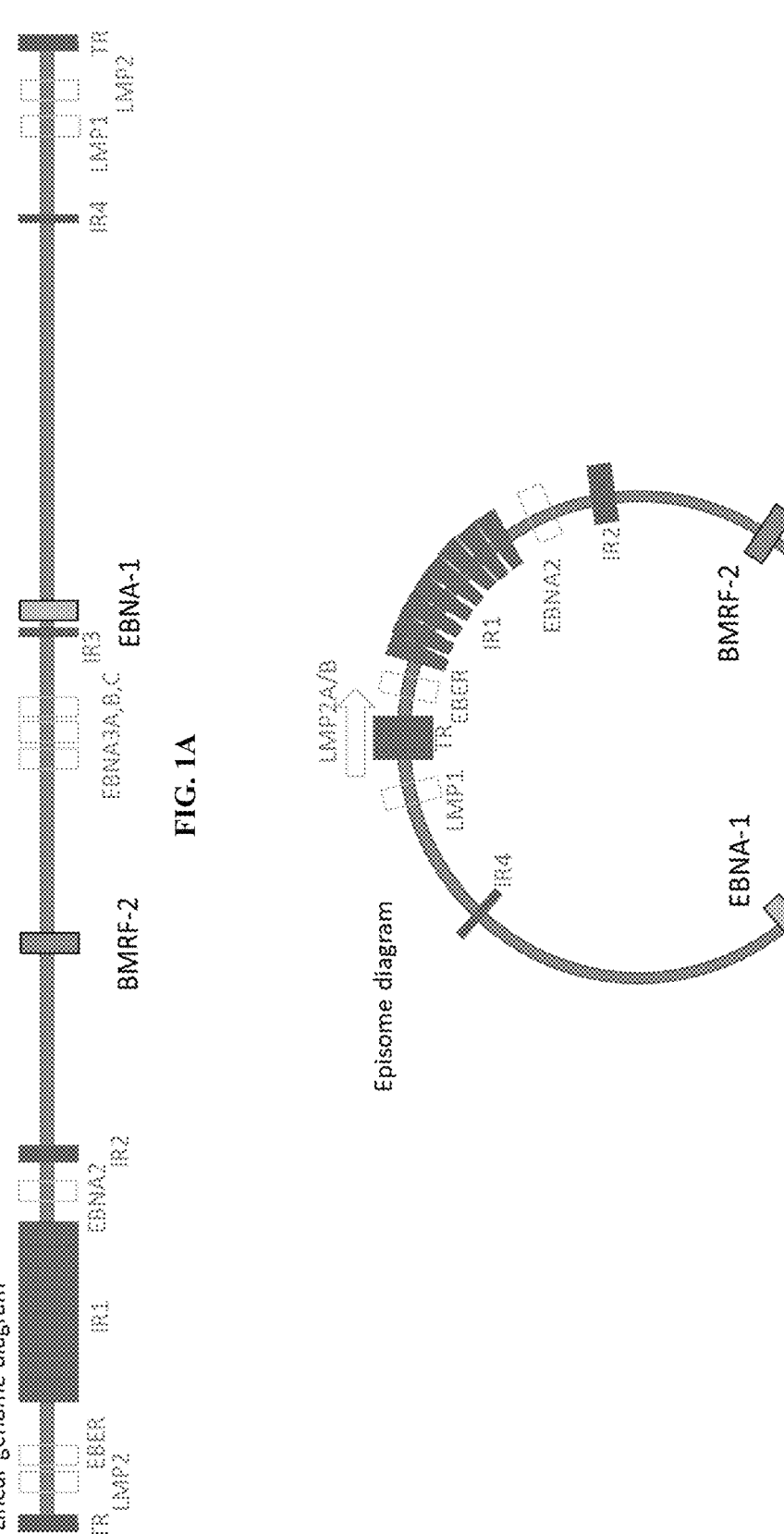
FIG. 1A shows a schematic diagram of the linear EBV genome (lytic form).
FIG. 1B shows a schematic diagram of the circular EBV genome (latent form). EBV is a double stranded DNA virus that is ~172 kb and larger. There are: (i) largely unique regions, (ii) internal repeat regions (IR1-IR4), (iii) terminal repeat (TR), (iv) Ori P., which is the origin for latent infection EBV episome replication, has plasmid maintenance and DNA replication activity, and (v) exons for latent EBV-induced membrane proteins and nuclear proteins.

Diagnosis of EBV infection by nucleic acid amplification provides a method for rapidly, accurately, reliably, specifically, and sensitively detecting and/or quantitating the EBV infection. A real-time PCR assay for detecting and/or quantitating EBV nucleic acids, including DNA and/or RNA, in a non-biological or biological sample is described herein. Primers and probes for detecting and/or quantitating EBV are provided, as are articles of manufacture or kits containing such primers and probes. The increased specificity and sensitivity of real-time PCR for detection of EBV compared to other methods, as well as the improved features of real-time PCR including sample containment and real-time detection and quantitating of the amplified product, make feasible the implementation of this technology for routine diagnosis of EBV infections in the clinical laboratory. Additionally, this technology may be employed for blood screening as well as for prognosis. This EBV detection assay may also be multiplexed with other assays for the detection of other nucleic acids, e.g., other bacteria and/or viruses, in parallel.

The present disclosure includes oligonucleotide primers and fluorescent labeled hydrolysis probes that hybridize to the EBV genome, in order to specifically identify EBV using, e.g., TaqMan® amplification and detection technology.

The disclosed methods may include performing at least one cycling step that includes amplifying one or more portions of the nucleic acid molecule gene target from a sample using one or more pairs of primers. "EBV primer(s)" as used herein refer to oligonucleotide primers that specifically anneal to nucleic acid sequences found in the EBV genome, and initiate DNA synthesis therefrom under appropriate conditions producing the respective amplification products. Examples of nucleic acid sequences found in the EBV genome, include nucleic acids within viral capsid protein region of the EBV genome, such as the VP2 region. Each of the discussed EBV primers anneals to a target such that at least a portion of each amplification product contains nucleic acid sequence corresponding to the target. The one or more amplification products are produced provided that one or more nucleic acid is present in the sample, thus the presence of the one or more amplification products is indicative of the presence of EBV in the sample. The amplification product should contain the nucleic acid sequences that are complementary to one or more detectable probes for EBV. "EBV probe(s)" as used herein refer to oligonucleotide probes that specifically anneal to nucleic acid sequences found in the EBV genome. Each cycling step includes an amplification step, a hybridization step, and a detection step, in which the sample is contacted with the one or more detectable EBV probes for detection of the presence or absence of EBV in the sample.

As used herein, the term "amplifying" refers to the process of synthesizing nucleic acid molecules that are complementary to one or both strands of a template nucleic acid molecule (e.g., nucleic acid molecules from the EBV genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released. The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus.* Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.*

25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, a 5-propynyl dU, a 5-propynyl dC, 7-deazadeoxyguanosine (deaza G (u-deaza)) and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection/Quantitation of EBV Target Nucleic Acid

The present disclosure provides methods to detect EBV by amplifying, for example, a portion of the EBV nucleic acid sequence. Specifically, primers and probes to amplify and detect and/or quantitate EBV nucleic acid molecule targets are provided by the embodiments in the present disclosure.

For detection and/or quantitation of EBV, primers and probes to amplify and detect/quantitate the EBV are provided. EBV nucleic acids other than those exemplified herein can also be used to detect EBV in a sample. For example, functional variants can be evaluated for specificity and/or sensitivity by those of skill in the art using routine methods. Representative functional variants can include, e.g., one or more deletions, insertions, and/or substitutions in the EBV nucleic acids disclosed herein.

More specifically, embodiments of the oligonucleotides each include a nucleic acid with a sequence selected from SEQ ID NOs:1-6, a substantially identical variant thereof in which the variant has at least, e.g., 80%, 90%, or 95% sequence identity to one of SEQ ID NOs:1-6, or a complement of SEQ ID NOs:1-6 and the variant.

TABLE 1

| Oligo Name | Oligo Type | SEQ ID NO: | Sequence | Modifications |
|---|---|---|---|---|
| | | | Oligonucleotides in EBV Test | |
| | | | BMFR2 #60 | |
| EBVBMRF 2F1181 | Forward Primer | 1 | CATCTGTTGTGGTATATTTCCTCK | K: t-Butyl Benzyl-dC |
| EBVBMRF 2P1222 | Probe | 2 | <FAM_Thr>CTGGGCQAAGACCGT GCTGTTTATCTCAATCTT<Phos> | Q: BHQ-2 |
| EBVBMRF 2R1278 | Reverse Primer | 3 | CGCTACCCCGCTAAAGTAJ | J: t-Butyl Benzyl-dA |
| | | | EBNA1 #77 | |
| EBVEBNA 1F3127 | Forward Primer | 4 | GCGTTGGAAAACATTAGCGAK | K: t-Butyl Benzyl-dC |
| EBVEBNA 1P3150 | Probe | 5 | <FAM_Thr>TTACCTQGGTGAGCA ATCAGACATGCGACGG<Phos> | Q: BHQ-2 |
| EBVEBNA 1R3222 | Reverse Primer | 6 | GTTGCTCCCATTCTTAGGTGAJ | J: t-Butyl Benzyl-dA |

In one embodiment, the above described sets of EBV primers and probes are used in order to provide for detection of EBV in a biological sample suspected of containing EBV (Table 1). The sets of primers and probes may comprise or consist of the primers and probes specific for the EBV nucleic acid sequences, comprising or consisting of the nucleic acid sequences of SEQ ID NOs:1-6. In another embodiment, the primers and probes for the EBV target comprise or consist of a functionally active variant of any of the primers and probes of SEQ ID NOs:1-6.

A functionally active variant of any of the primers and/or probes of SEQ ID NOs:1-6 may be identified by using the primers and/or probes in the disclosed methods. A functionally active variant of a primer and/or probe of any of the SEQ ID NOs:1-6 pertains to a primer and/or probe which provide a similar or higher specificity and sensitivity in the described method or kit as compared to the respective sequence of SEQ ID NOs:1-6.

The variant may, e.g., vary from the sequence of SEQ ID NOs:1-6 by one or more nucleotide additions, deletions or substitutions such as one or more nucleotide additions, deletions or substitutions at the 5' end and/or the 3' end of the respective sequence of SEQ ID NOs:1-6. As detailed above, a primer and/or probe may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the EBV target, e.g., nucleic acids encoding alternative portions of EBV can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of EBV. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a EBV (target) nucleic acid. A "probe" can be referred to as a "detection probe" meaning that it detects the target nucleic acid. In some embodiments, the described EBV probes can be labeled with at least one fluorescent label. In one embodiment, the EBV probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs:2 and/or 5.

Designing oligonucleotides to be used as probes can be performed in a manner similar to the design of primers. Embodiments may use a single probe or a pair of probes for detection of the amplification product. Depending on the embodiment, the probe(s) used may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of EBV primers and probes nucleic acid molecules (e.g., SEQ ID NOs:1, 2, 3, 4, and 5). Constructs can be used, for example, as control template nucleic acid molecules. Vectors suitable for use are commercially available and/or produced by recombinant nucleic acid technology methods routine in the art. EBV nucleic acid molecules can be obtained, for example, by chemical synthesis, direct cloning from EBV, or by nucleic acid amplification.

Constructs suitable for use in the methods typically include, in addition to the EBV nucleic acid molecules (e.g., a nucleic acid molecule that contains one or more sequences of SEQ ID NOs:1-6), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing EBV nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens,* and *Bacillus subtilis.* Eukaryotic hosts include yeasts such as *S. cerevisiae, S. pombe, Pichia pastoris,* mammalian cells such as COS cells or Chinese hamster ovary (CHO) cells, insect cells, and plant cells such as *Arabidopsis thaliana* and *Nicotiana tabacum.* A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described EBV nucleic acid sequences (e.g., SEQ ID NOs:1, 3, 4, and 6). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, or the mRNA produced by a DNA virus, such as EBV, is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ EBV nucleic acid such as RNA or DNA (cDNA). The template nucleic acid need not be purified; it may be a minor fraction of a complex mixture, such as EBV nucleic acid contained in human cells. EBV nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs:1, 2, 4, and 5) are combined with PCR reagents under reaction conditions that induce primer extension. For example, chain extension reactions generally include 50 mM KCl, 10 mM Tris-HCl (pH 8.3), 15 mM MgCl$_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target EBV nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times. Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety or dye (e.g., HEX or FAM) and a corresponding quencher (e.g., BlackHole QuencherTM (BHQ) (such as BHQ-2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quencher™ (BHQ) (such as BHQ2), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the EBV target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phyco-erythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, VA)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif)), or 3'-amino-CPGs that require coupling of a fluorescein-NHS-ester after oligonucleotide synthesis.

Detection of EBV Amplified Product (Amplicon)

The present disclosure provides methods for detecting the presence or absence of EBV in a biological or non-biological sample. Methods provided avoid problems of sample contamination, false negatives, and false positives. The methods include performing at least one cycling step that includes amplifying a portion of EBV target nucleic acid molecules from a sample using one or more pairs of EBV primers, and a FRET detecting step. Multiple cycling steps are performed, preferably in a thermocycler. Methods can be performed using the EBV primers and probes to detect the presence of EBV, and the detection of EBV indicates the presence of EBV in the sample. As described herein, amplification products can be detected using labeled hybridization probes that take advantage of FRET technology. One FRET format utilizes TaqMan® technology to detect the presence or absence of an amplification product, and hence, the presence or absence of EBV. TaqMan® technology utilizes one single-stranded hybridization probe labeled with, e.g., one fluorescent moiety or dye (e.g., HEX or FAM) and one quencher (e.g., BHQ-2), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of EBV in the sample. Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of EBV genomes). If amplification of EBV target nucleic acid occurs and an amplification product is produced, the step of hybridizing results in a detectable signal based upon FRET between the members of the pair of probes.

Generally, the presence of FRET indicates the presence of EBV in the sample, and the absence of FRET indicates the absence of EBV in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to whole blood, respiratory specimens, urine, fecal specimens, blood specimens, plasma, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release EBV nucleic acid or in some cases, the biological sample can be contacted directly with the PCR reaction components and the appropriate oligonucleotides. In some instances, the biological sample is whole blood. When whole blood is typically collected, it is often collected in vessels containing anticoagulants, such as heparin, citrate, or EDTA, which enables the whole blood to be stored at suitable temperatures. However, under such conditions, the nucleic acids within the whole blood undergo considerable amount of degradation. Therefore, it may be advantageous to collect the blood in a reagent that will lyse, denature, and stabilize whole blood components, including nucleic acids, such as a nucleic acid-stabilizing solution. In such cases, the nucleic acids can be better preserved and stabilized for subsequent isolation and analysis, such as by nucleic acid test, such as PCR. Such nucleic acid-stabilizing solution are well known in the art, including, but not limited to, cobas PCR media, which contains 4.2 M guanadinium salt (GuHC1) and 50 mM Tris, at a pH of 7.5.

The sample can be collected by any method or device designed to adequately hold and store the sample prior to analysis. Such methods and devices are well known in the art. In the case that the sample is a biological sample, such as whole blood, the method or device may include a blood collection vessel. Such a blood collection vessel is well known in the art, and may include, for example, a blood collection tube. In many cases, it may be advantageous to use a blood collection tube wherein the blood collection vessel is under pressure in the space intended for sample uptake, such as a blood vessel with an evacuated chamber, such as a vacutainer blood collection tube. Such blood collection tubes with an evacuated chamber, such as a vacutainer blood collection tube are well known in the art. It may further be advantageous to collect the blood in a blood collection vessel, with or without an evacuated chamber, that contains within it, a solution that will lyse, denature, and stabilize whole blood components, including nucleic acids, such as a nucleic acid-stabilizing solution, such that the whole blood being drawn immediately contacts the nucleic acid-stabilizing solution in the blood collection vessel.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the EBV probes from the EBV amplification products can confirm the presence or absence of EBV in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control(s) can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

The LightCycler® 480 II Real-Time PCR System can also be operated using a PC workstation. The instrument has a thermal block cycler and heating and cooling is achieved using Peltier elements. Fluorescent signals from the samples are obtained from the 96-well plate using a high-intensity Xenon lamp which emits light across a broad spectrum. Flexible combination of the built-in filters for specific excitation and emission allows the use of a variety of fluorescent dyes and detection formats. The software can display the fluorescence signals and calculate CT values, and the data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect EBV. An article of manufacture can include primers and probes used to detect the EBV gene target, together with suitable packaging materials. Representative primers and probes for detection of EBV are capable of hybridizing to EBV target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to EBV target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the EBV probes. Examples of suitable FRET donor fluorescent moieties and corresponding acceptor fluorescent moieties are provided above.

Articles of manufacture can also contain a package insert or package label having instructions thereon for using the EBV primers and probes to detect EBV in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure also provide for a set of primers and one or more detectable probes for the detection of EBV in a sample.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

The test was a fully automated sample preparation (nucleic acid extraction and purification) followed by PCR amplification and detection. The system used was the cobas® 6800/8800 System, which consisted of a sample supply module, the transfer module, the processing module, and the analytic module. Automated data management was performed by the cobas® 6800/8800 System. The master mix contained detection probes which were specific for EBV and control nucleic acids. The specific EBV and control detection probes were each labeled with one of two unique fluorescent dyes which act as a reporter. Each probe also had a second dye which acted as a quencher. The reporter dye is measured at a defined wavelength, thus permitting detection and discrimination of the amplified EBV target and the control. The fluorescent signal of the intact probes was suppressed by the quencher dye. During the PCR amplification step, hybridization of the probes to the specific single-stranded DNA template resulted in cleavage by the 5' to 3' nuclease activity of the DNA polymerase resulting in separation of the reporter and quencher dyes, and the generation of fluorescent signal. With each PCR cycle, increasing amounts of cleaved probes were generated and the cumulative signal of the reporter dye was concomitantly increased. Because the two specific reporter dyes are measured at defined wavelengths, simultaneous detection and discrimination of the amplified EBV target and the control was possible.

The primers and probes for the EBV test were designed by seeding primers and probes along the genome in the most conserved regions based on the alignment. One set of oligonucleotides (SEQ ID NOs:1-3) was designed to detect the BMRF2 region of the EBV genome. Another set of oligonucleotides (SEQ ID NOs:4-6) was designed to detect the EBNA1 region of the EBV genome.

Each set of oligonucleotides (or primers/probes) can be used in singleplex in its own reaction to amplify and detect the particular target region of interest (i.e., BMRF2 and EBNA1). However, the set of oligonucleotides can also be combined in a dual target assay, whereby in a single real-time PCR reaction, both BMRF2 and EBNA1 are amplified and detected in the sample, because the reaction mixture contains both sets of oligonucleotides (SEQ ID NOs:1-3 and SEQ ID NOs:4-6). For detection of the BMRF2 region, the forward primer corresponds to the nucleic acid sequence of SEQ ID NO:1, the reverse primer corresponds to the nucleic acid sequence of SEQ ID NO:3, and the probe corresponds to the nucleic acid sequence of SEQ ID NO:2. For detection of the EBNA1 region, the forward primer corresponds to the nucleic acid sequence of SEQ ID NO:4, the reverse primer corresponds to the nucleic acid sequence of SEQ ID NO:6, and the probe corresponds to the nucleic acid sequence of SEQ ID NO:5. These oligonucleotides can be employed in individual assays for detection of the BMRF2 region of EBV (using SEQ ID NOs:1-3) and for detection of the EBNA1 region of EBV (using SEQ ID NOs:4-6). Alternatively, the oligonucleotides can be used in a dual target assay wherein the oligonucleotides (SEQ ID NOs:1-6) simultaneously detect the BMRF2 region and the EBNA1 region of EBV within the same sample. There are certain advantages to a dual target assay, in that in the event that one or more of the targeted region contains a mismatch or an error of some sort, or if one of the reactions experiences an error, there is another target and another reaction that can occur.

Example 1

Design of Primers and Probes for Detection of EBV by Real-Time PCR

Figure 2:
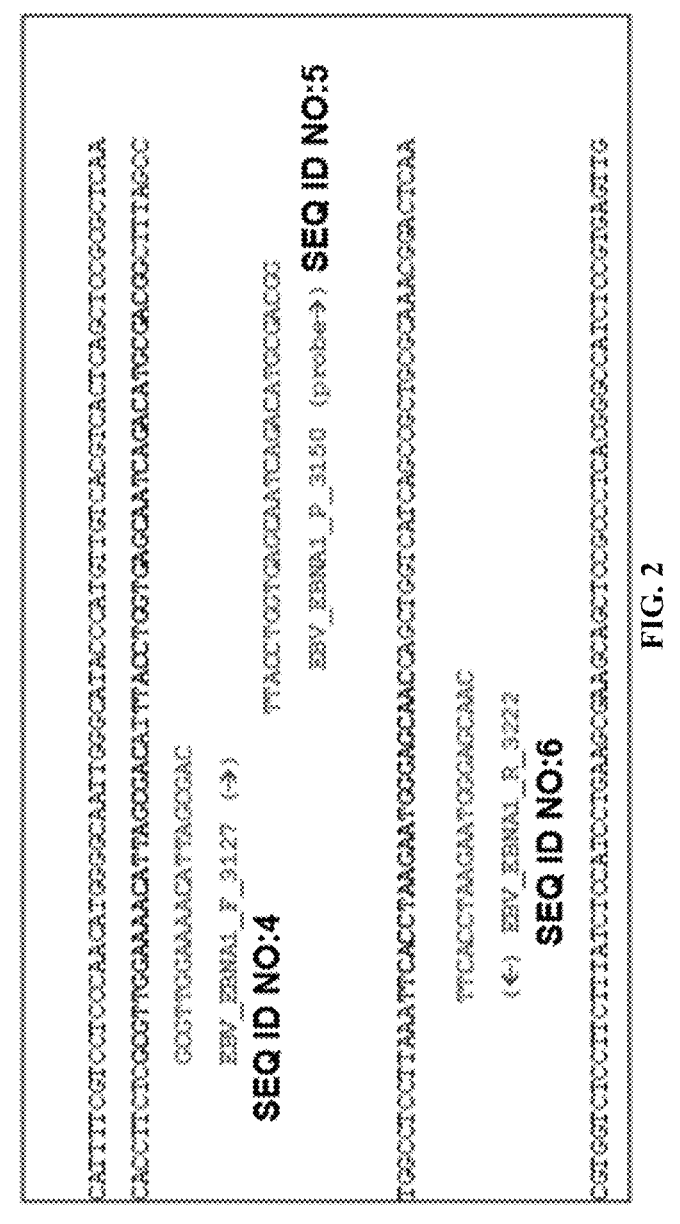
Figure 3:
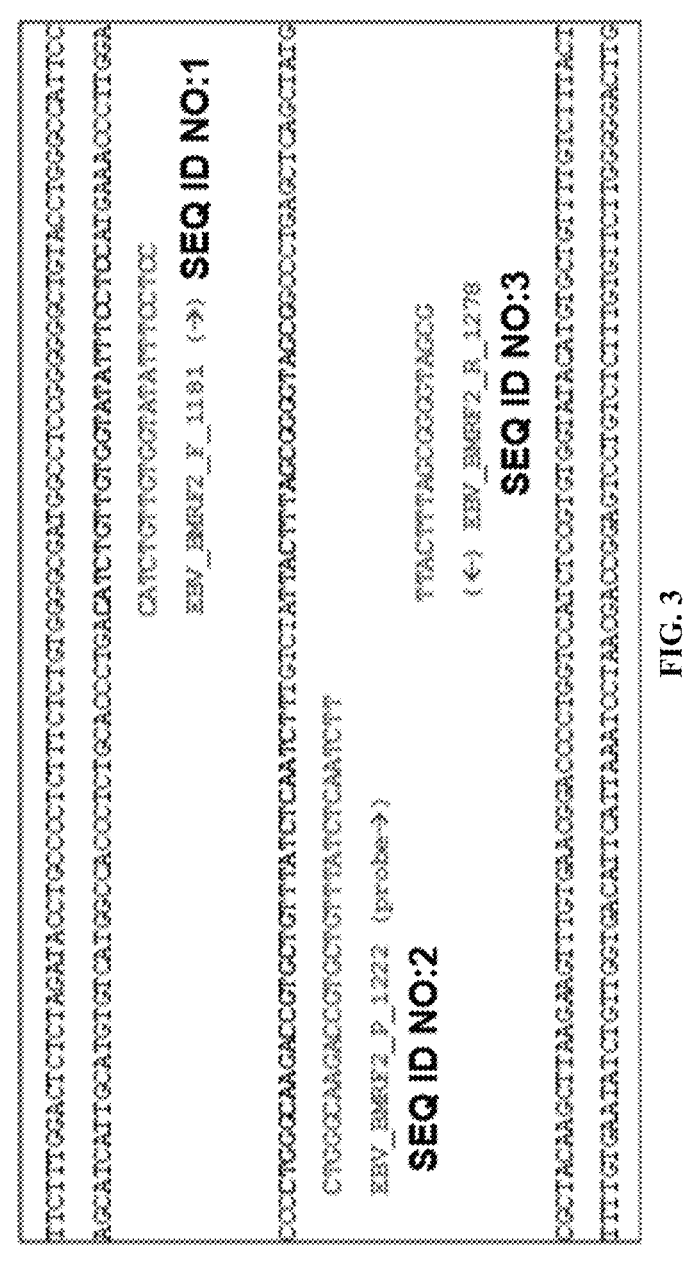

The EBV nucleic acid test was designed with two targets in mind. The two targets chosen were BMRF2 and EBNA1, and are shown in FIG. 1. These candidates could be used individually or together duplexed in a dual target assay. If used as a dual target assay, two sets of primers and probe are employed (each set detecting either EBNA1 or BMRF2). As shown in Table 1, above, the primers for BMRF2 target have the nucleic acid sequence SEQ ID NOs:1 and 3, and the probe for BMRF2 target has the nucleic acid sequence of SEQ ID NO:2. Also, as shown in Table 1, above, the primers for EBNA1 target have the nucleic acid sequence SEQ ID NOs:4 and 6, and the probe for EBNA1 target has the nucleic acid sequence of SEQ ID NO:5. The amplicon generated by the primers targeting BMRF2 is a 96 base pair long amplicon, and is shown in FIG. 2 (along with locations where the primers and probes overlap the amplicon). The amplicon generated by the primers targeting EBNA1 is a 98 base pair long amplicon, and is shown in FIG. 3 (along with locations where the primers and probes overlap the amplicon).

Example 2

EBV Primers and Probes Detect BMRF2 and EBNA-1 of EBV in Real-Time PCR Assay The EBV nucleic acid test was tested using primers/probes for detecting BMRF2 (SEQ ID NOs:1-3) and EBNA1 (SEQ ID NOs:4-6). A full process of the EBV assay was run. Four types of EBV-containing samples were employed: (1) EBV-infected Raji cells extracts spiked into EBV-negative plasma; (2) extracted EBV DNA (extracted from a B95-8 cell line from Advanced Biotechnologies (Catalog No. 17-926-500)); (3) Qnostics EBV Analytic Panel (EBV1604009C); and (4) the 1$^{st}$ WHO International Standard for EBV. Reagents used include cobas® 6800/8800 generic PCR Master Mix, with the profile and conditions for use with the cobas® 6800/8800, and using TaqMan® amplification and detection technology. The final concentration of oligonucleotides in the master mix was 0.3 µM for primers and 0.1 µM for probes. The cobas® 6800/8800 PCR Profile employed is depicted in Table 2, below:

TABLE 2

| cobas ® 6800/8800 PCR Profile | | | | |
|---|---|---|---|---|
| Step | Cycles | Target (° C.) | Hold time (hh:mm:ss) | Ramp |
| Pre-PCR | 1 | 50 | 00:02:00 | 4.4 |
| | | 94 | 00.00:05 | 4.4 |
| | | 55 | 00:02:00 | 2.2 |
| | | 60 | 00 06:00 | 4.4 |
| | | 65 | 00:04:00 | 4.4 |
| 1. Meas | 5 | 95 | 00:00:05 | 4.4 |
| | | 55 | 00 00 30 | 2.2 |
| 2. Meas | 45 | 91 | 00:00:05 | 4.4 |
| | | 58 | 00:00:25 | 2.2 |
| Post | 1 | 40 | 00:02:00 | 2.2 |

The results are shown below, in Table 3, below.

TABLE 3

|  | CT | RFI | AFI |
|---|---|---|---|
| WHO, 8E5 IU/mL | 19.21 | 16.27 | 48.78 |
| WHO, 8E4 IU/mL | 22.67 | 16.10 | 50.66 |
| WHO, 8E3 IU/mL | 25.94 | 15.97 | 53.94 |
| WHO, 8E2 IU/mL(clot) | NaN | 1.08 | 0.01 |
| WHO, 8E1 IU/mL | 32.93 | 12.22 | 25.50 |
| WHO, 8E0 IU/mL | 36.07 | 11.24 | 36.64 |
| Q_C, 8E3 IU/mL | 25.12 | 16.13 | 45.87 |
| Q_C, 8E2 IU/mL | 28.94 | 15.66 | 41.89 |
| Q_C, 89E1 IU/mL | 32.43 | 15.04 | 43.79 |
| Q_C, 8E0 IU/mL | 35.63 | 10.47 | 31.30 |
| Raji, 100c (400 c/mL) | 30.36 | 14.64 | 45.77 |
| Raji, 10c (40 c/mL) | 34.37 | 12.49 | 36.25 |
| Raji, 1c (4c/mL) | 36.15 | 9.70 | 26.49 |
| Raji, 0.1c (0.4c/mL) | NaN | 1.01 | 0.02 |
| Ad_B95-8, 500c (2E4c/mL) | 26.5 | 16.08 | 45.72 |
| Ad_B95-8, 500c (2E3c/mL) | 30.02 | 15.77 | 45.88 |
| Ad_B95-8, 50c (2E2c/mL) | 33.37 | 13.55 | 37.41 |
| Ad_B95-8, 5c (2E1c/mL) | 35.81 | 10.74 | 26.76 |
| Neg_plasma | NaN | 1.01 | 0.04 |
| Neg_plasma | NaN | 1.02 | 0.05 |

Figure 4A:
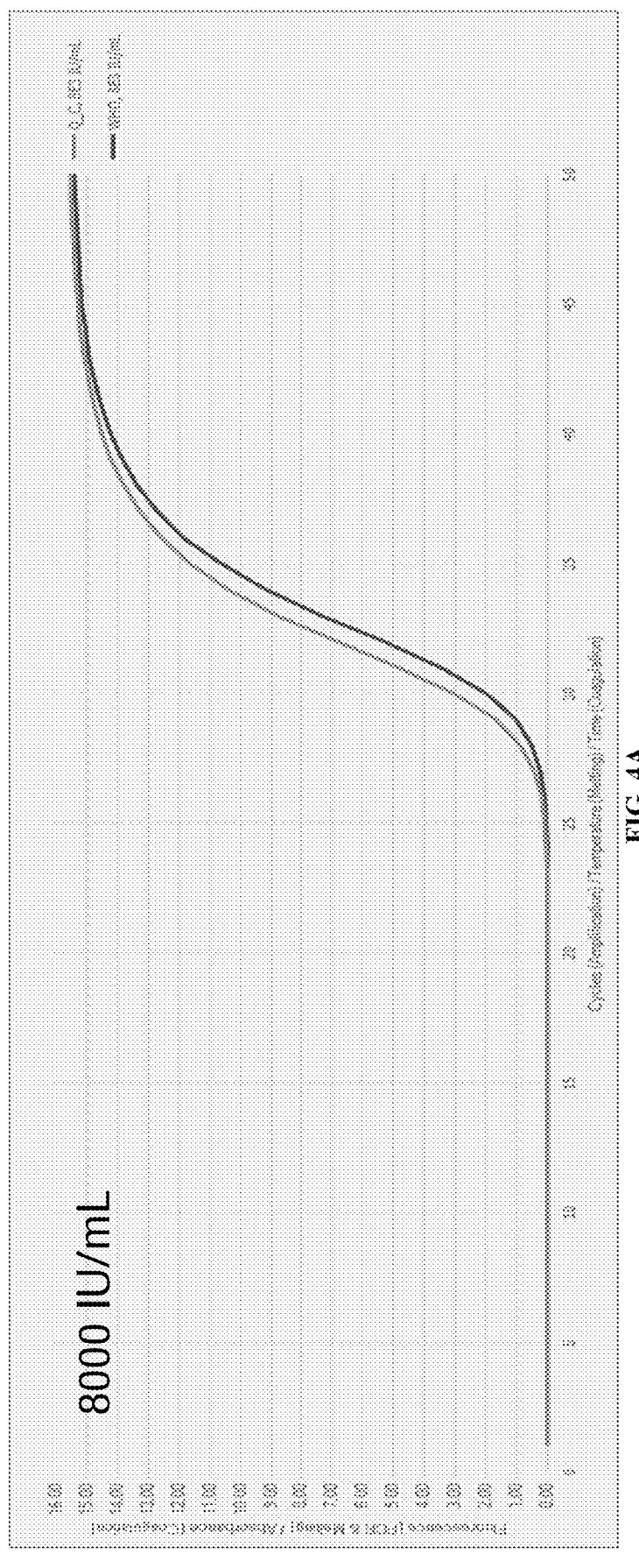
FIGS. 4A-C shows PCR growth curves of a dilution series of the performance of the assay on a Qnostics EBV Analytic Panel (Qnostics Catalog No. EBVAQP03-C) versus a WHO Standard for EBV (NIB SC code 09/260), at 8 (FIG. 4C), 80 (FIG. 4B), and 8,000 IU/ml (FIG. 4A). Other EBV sample types were also tested, such as extracted EBV DNA and Raji cell line DNA spiked into EBV-negative plasma (data not shown).
Figure 4B:
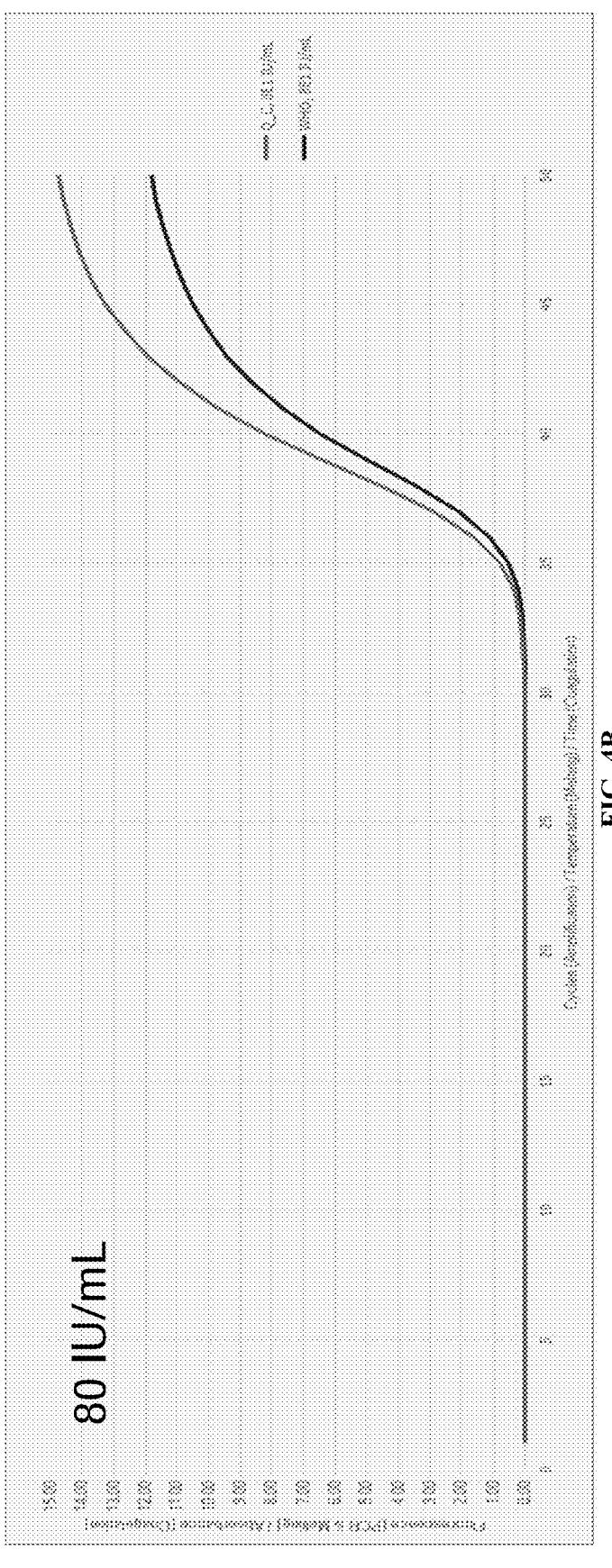
Figure 4C:
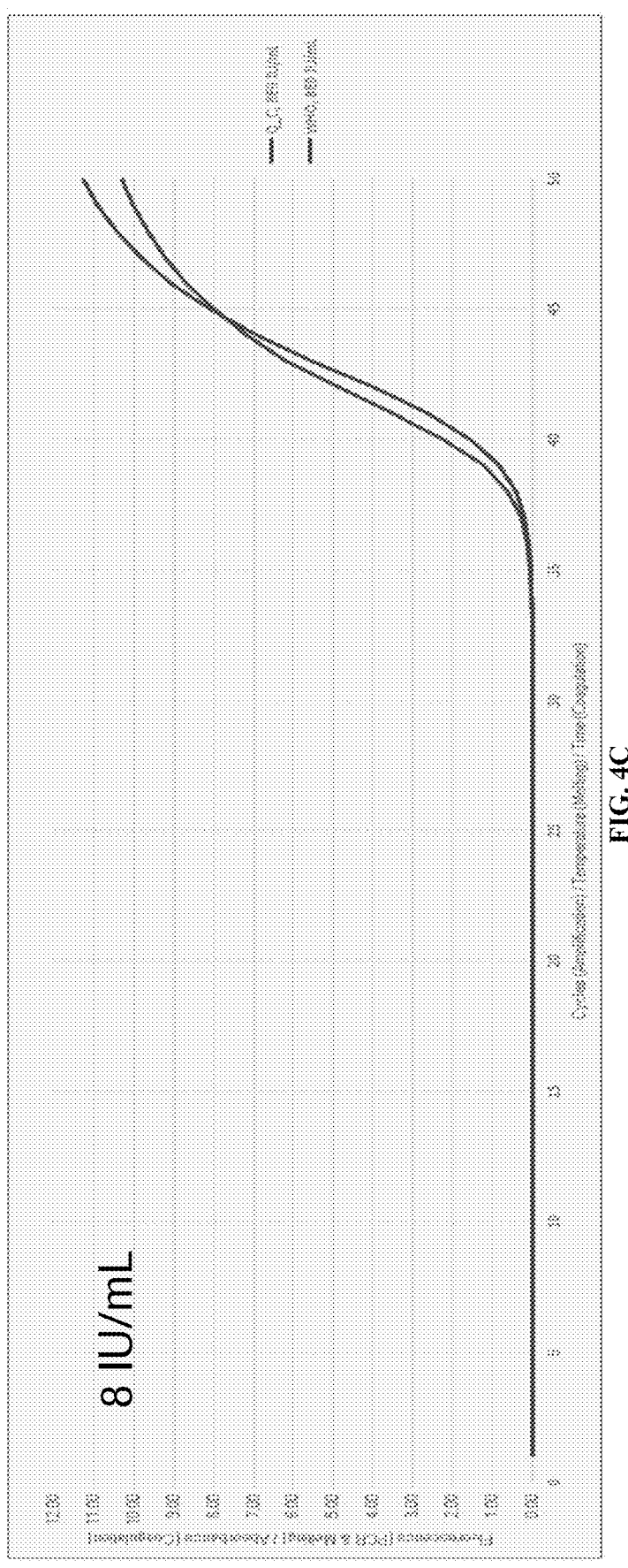
Figure 5A:
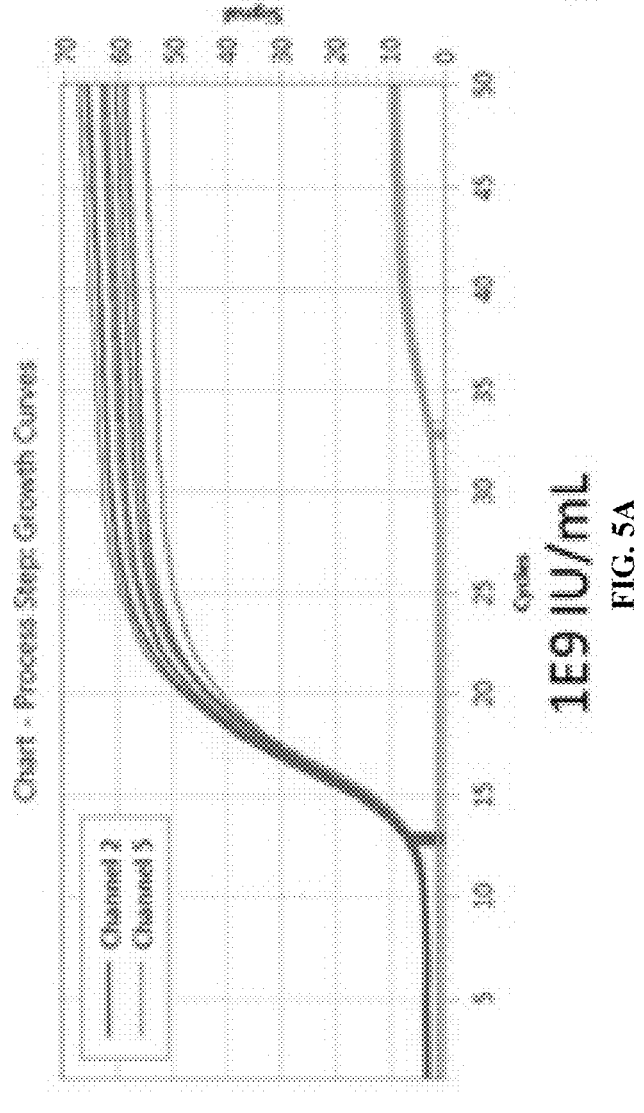
FIGS. 5A-5L shows PCR growth curves of a dilution series of the performance of the multiplexed assay on a cell culture derived material (from 1E4 IU/mL to 20 IU/mL) (FIGS. 5H-5L) and for a control template (from 1E9 IU/mL to 1E3 IU/mL) (FIGS. 5A-5G). Channel 2 shows the dual target EBV assay and channel 5 is an internal control reaction.
Figure 5B:
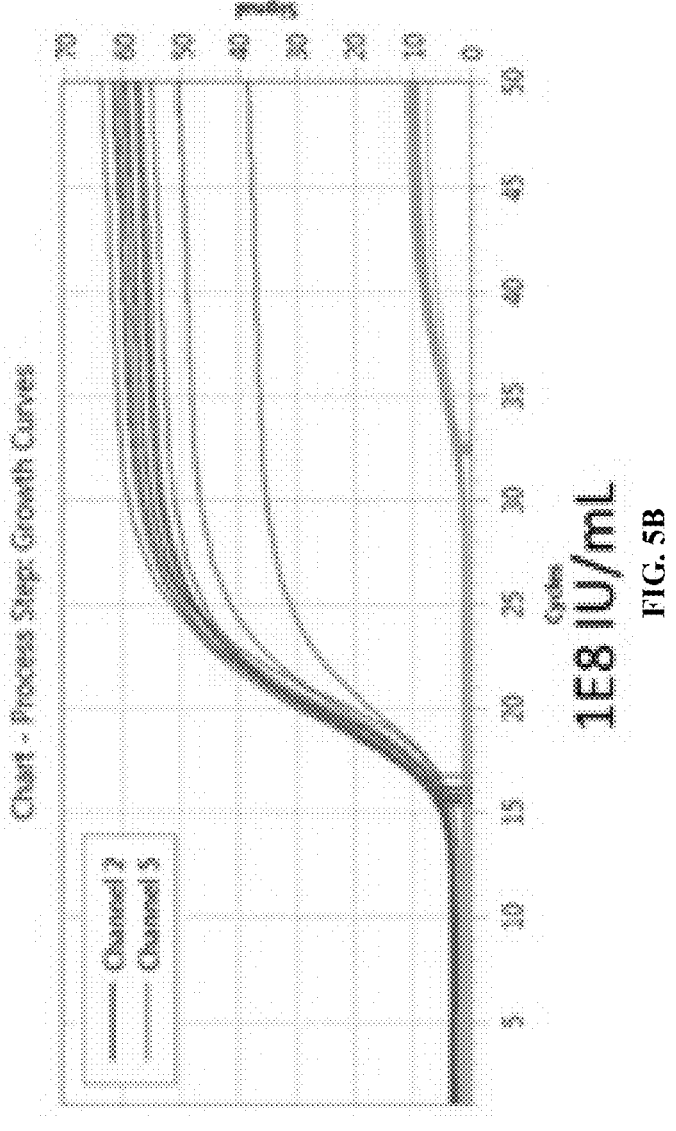
Figure 5C:
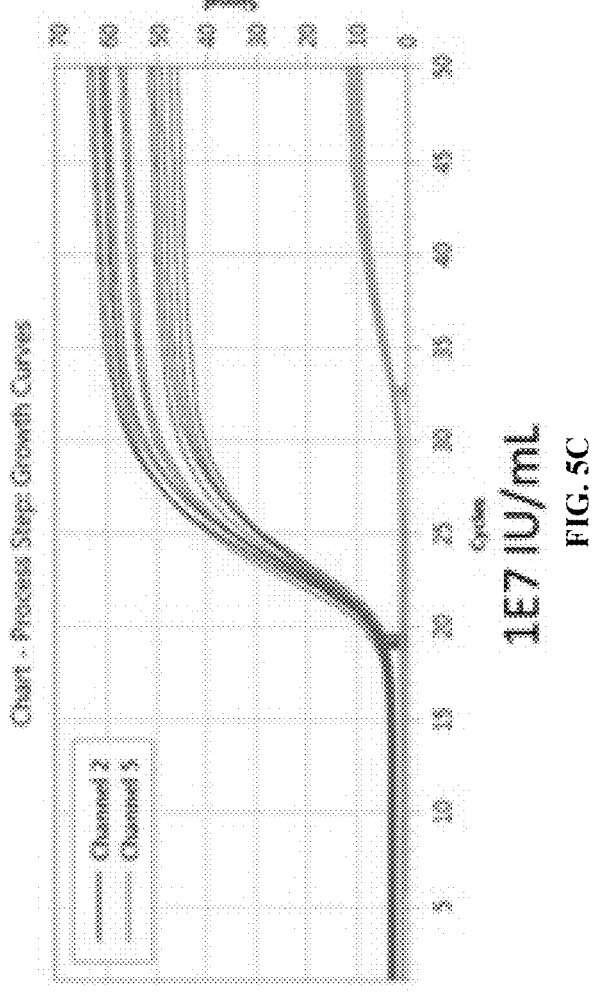
Figure 5D:
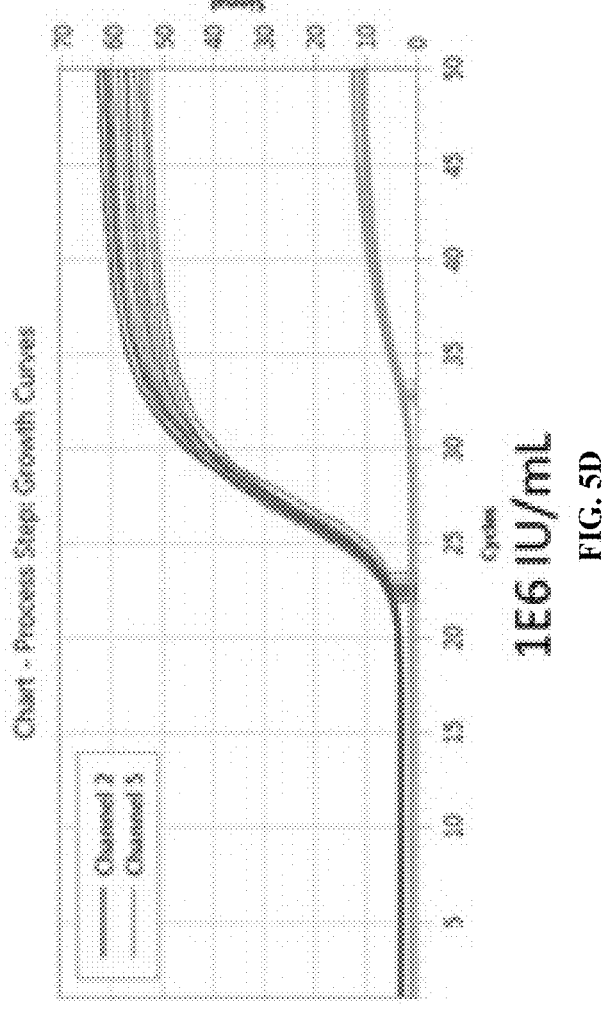
Figure 5E:
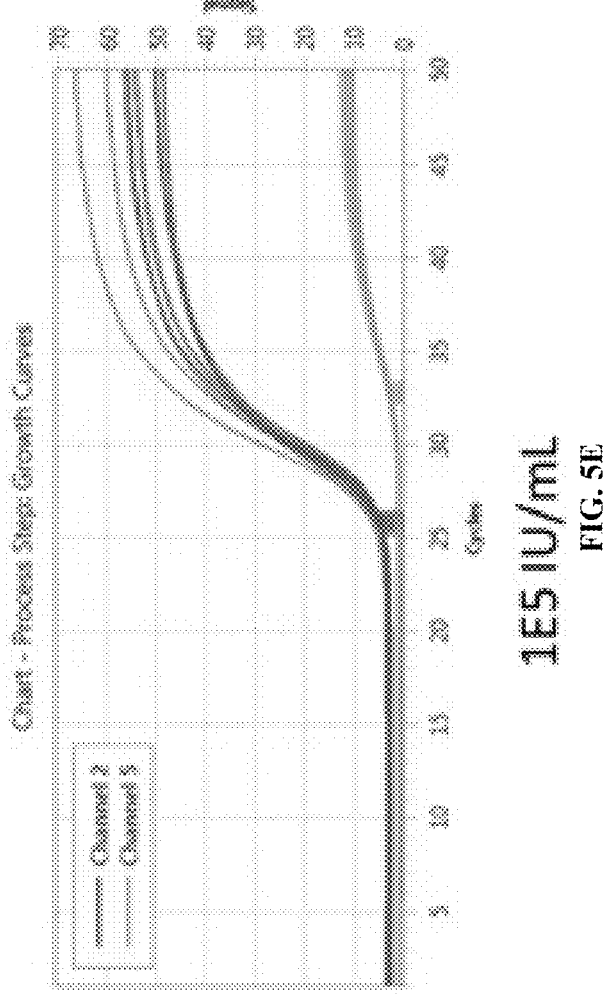
Figure 5F:
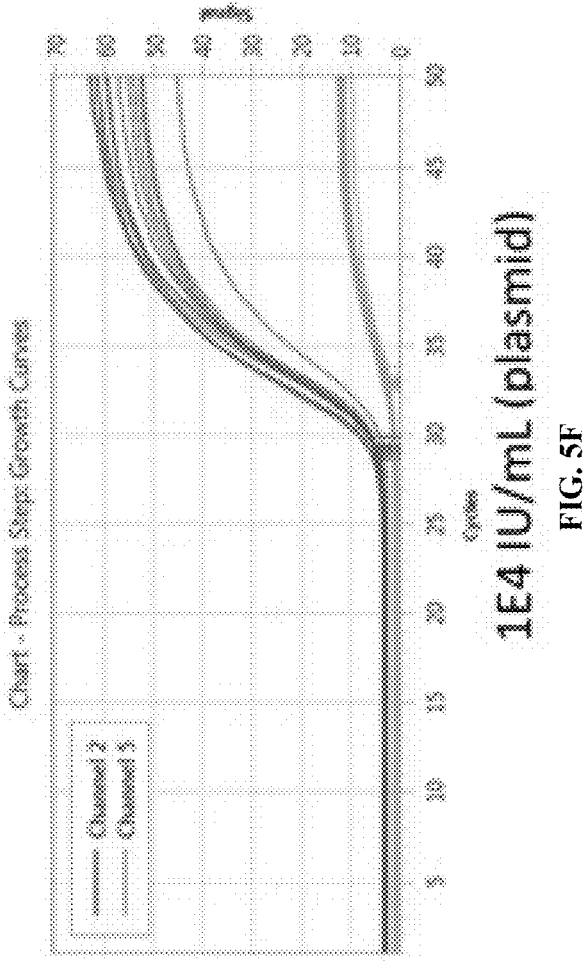
Figure 5G:
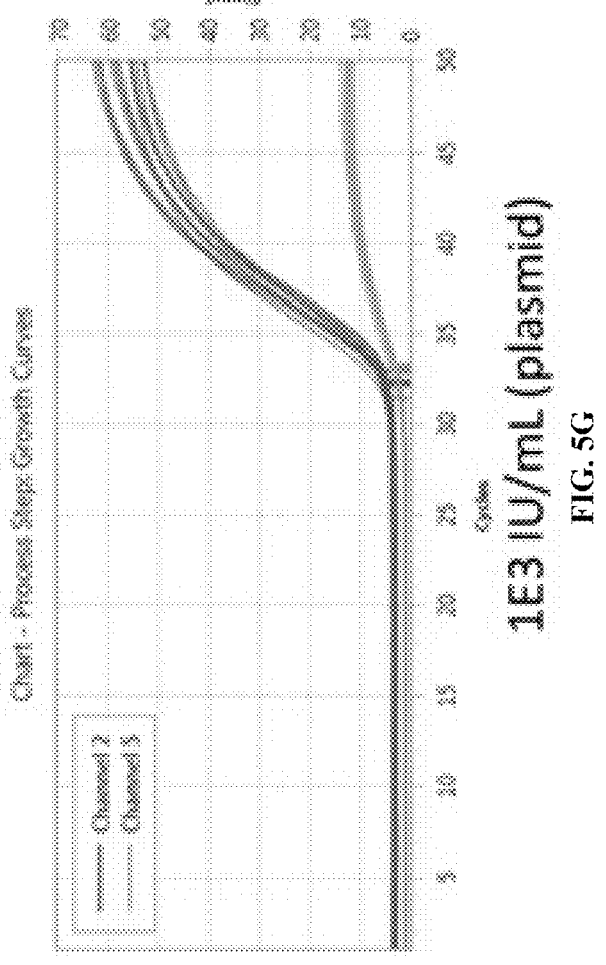
Figure 5H:
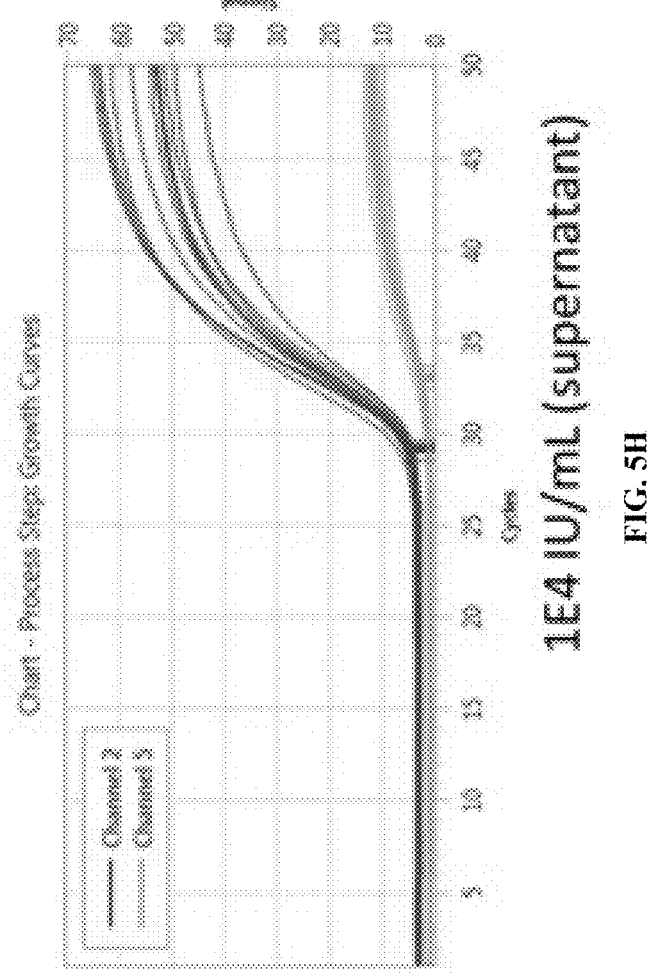
Figure 5I:
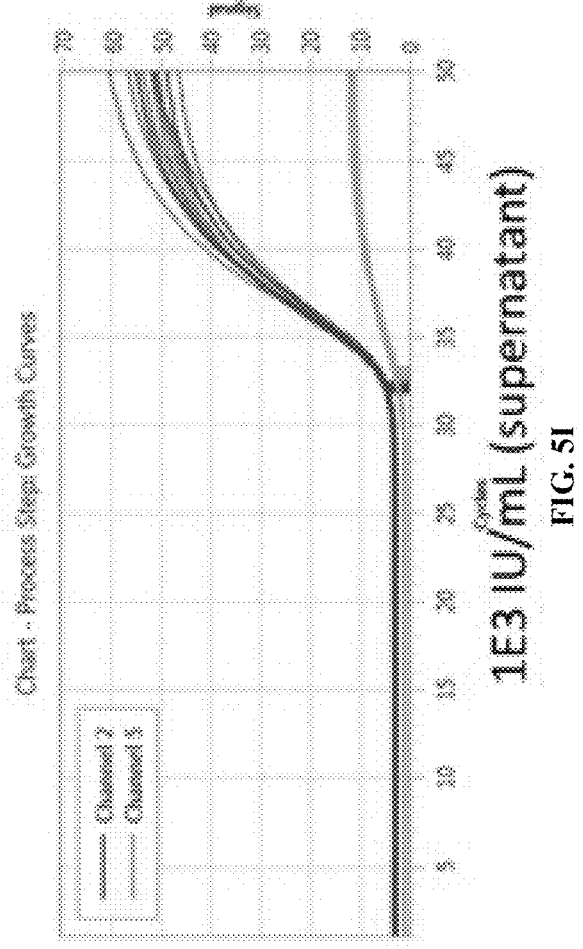
Figure 5J:
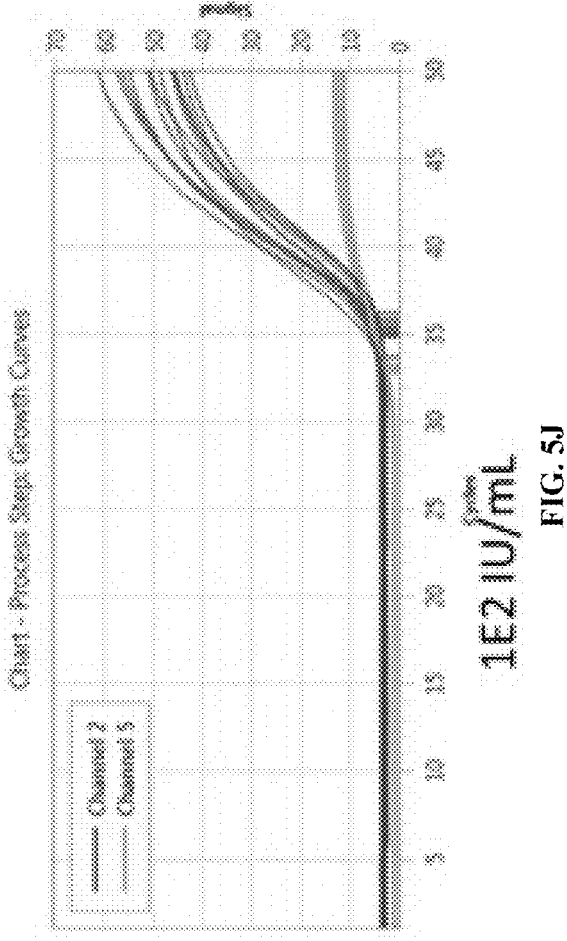
Figure 5K:
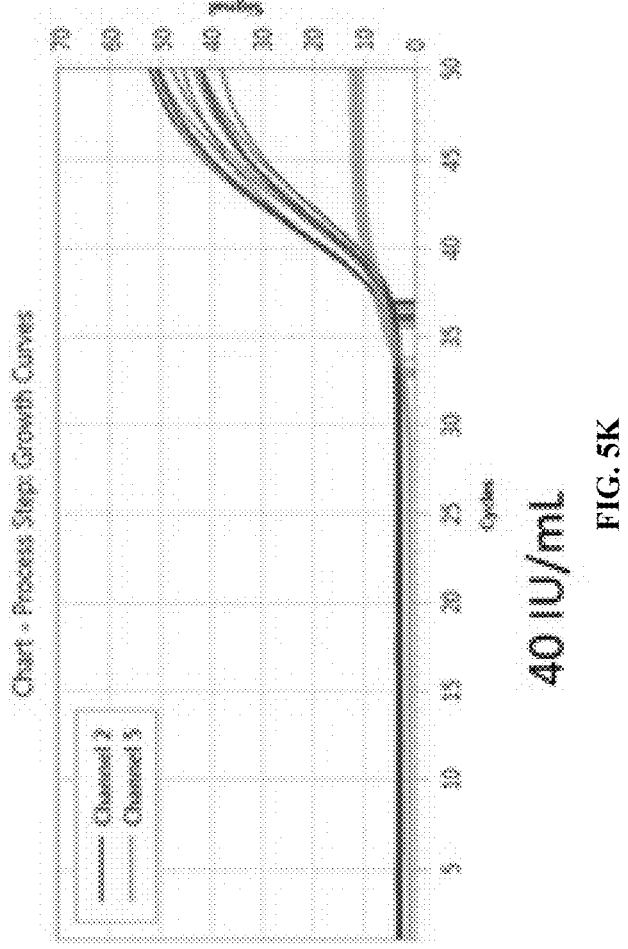
Figure 5L:
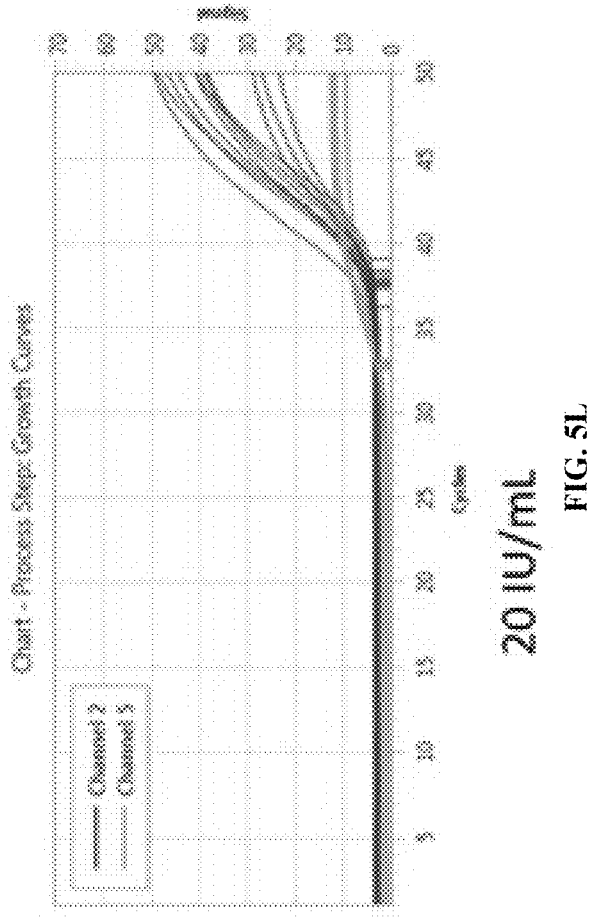

The 1$^{st}$ WHO International Standard for EBV stock was at a concentration of 5×10$^6$ IU/ml, while the Qnostics EBV Analytic Panel has a series of samples of varying concentrations. Serial dilutions of the WHO material and an additional dilution of an aliquot of the Qnostics panel were made. The Qnostics EBV Analytic Panel was analyzed at 8,000, 800, 80, and 8 IU/ml, whereas the 1$^{st}$ WHO International Standard for EBV was analyzed at 800,000, 80,000, 8,000, 800, 80, and 8 IU/ml. The results for the Qnostics EBV Analytic Panel and the 1$^{st}$ WHO International Standard for EBV are shown in FIGS. 4A-4C. Another full process test of the dual target assay was done on both a cell culture derived viral material (Exact diagnostics supernatant), as depicted in FIGS. 5H-5L, and a control plasmid material containing both target regions, as depicted in FIGS. 5A-5G. These two materials were each diluted and the estimated titers overlapped at 1E4 IU/mL and 1E3 IU/mL where both materials could be tested. The resulting growth curves were shown in FIG. 5A-5L. These data and results demonstrate that the primers and probes (SEQ ID NOs:1-6) amplify and detect the presence of EBV in varied sample types including commercial and international standards.

Figure 6A:
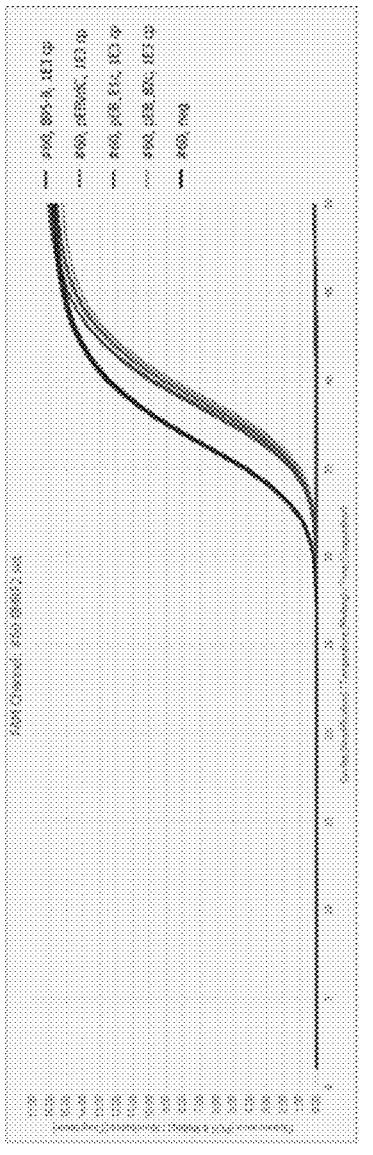
FIGS. 6A and 6B show PCR growth curves for separate reactions for EBNA1 (FIG. 6A and BMRF2 (FIG. 6B on plasmid templates containing individual targets (E1c, B2c) or both targets (dC), as well as a B95-8 cell line extraction (containing copies of EBV DNA). These studies demonstrate that the dual target EBNA1 and BMRF2 EBV assays are efficient and specifically identifying EBNA1 and BMRF2 EBV nucleic acid.
Figure 6B:
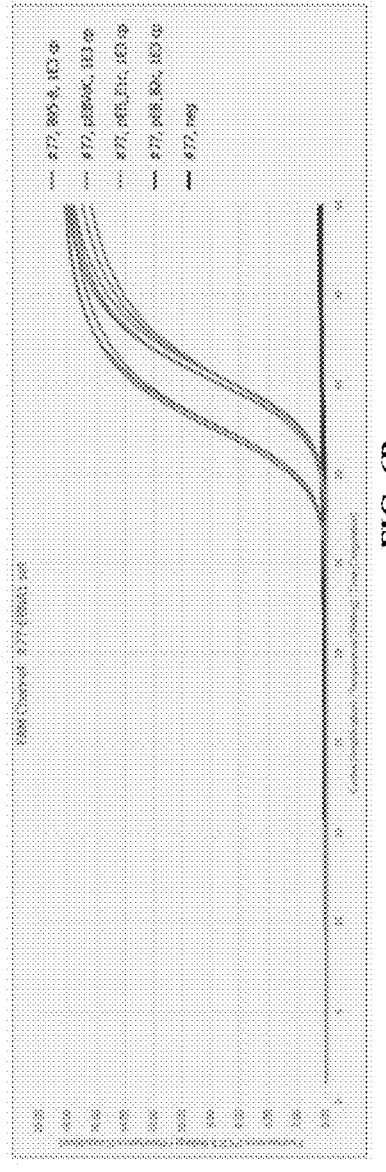

The EBV dual target and single target plasmids were tested using the single target EBV primers and probes. Results are shown in FIGS. 6A and 6B, which demonstrate that the positive control templates for both BMRF2 and EBNA1 are amplified and detected by the respective EBV primers/probes for BMRF2 (SEQ ID NOs:1-3) and for EBNA1 (SEQ ID NOs:4-6), but each single-target control plasmid does not cross-react with the other target, while a dual-target control plasmid and viral genomic DNA extract are amplified by both oligo sets.

Figure 7:
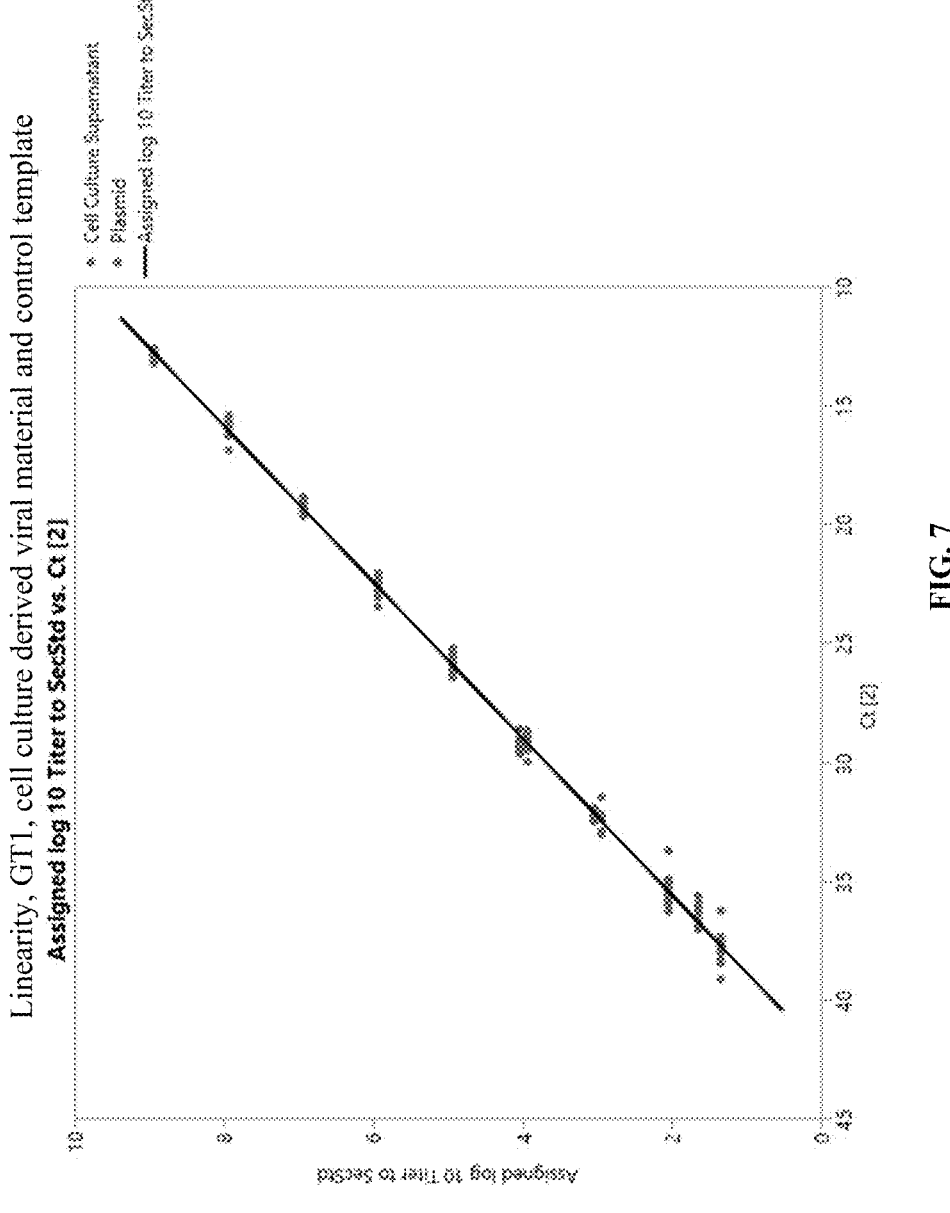
FIG. 7 shows Linearity data for the dual target assay on a genotype 1 cell culture derived material and for a control template.
Figure 8:
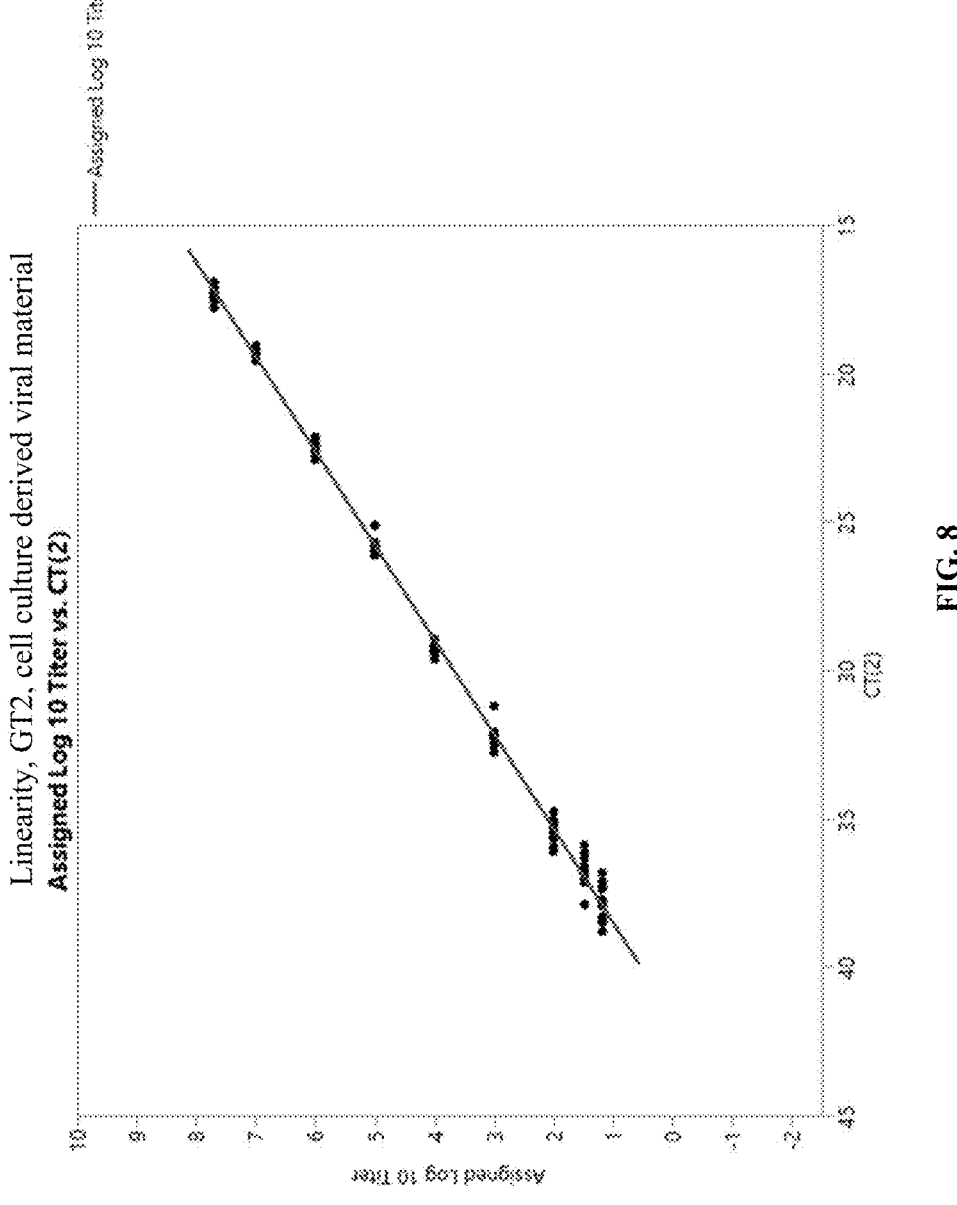
FIG. 8 shows Linearity data for the dual target assay on a genotype 2 EBV-containing cell culture derived material.

A linearity test of the dual target assay was done on EBV genotype 1 and EBV genotype 2 materials. For genotype 1 both a cell culture derived viral material (Exact diagnostics) and a control plasmid material containing both target regions were used, the estimated titers of which overlapped. For genotype 2 a cell culture derived viral material (ATCC strain P3) was tested. Results are shown in FIGS. 7 and 8. These data and results show that the assay detects and could be used for quantitation of both EBV genotype 1 and genotype 2.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The invention claimed is:

1. A method for detecting one or more target nucleic acids of Epstein Barr Virus (EBV) in a sample, wherein the method comprises:

(a) providing a sample;

(b) performing an amplification step comprising contacting the sample with one or more set of primers to produce an amplification product, if the one or more target nucleic acids of EBV is present in the sample;

(c) performing a hybridization step, comprising contacting the amplification product, if the one or more target nucleic acids of EBV is present in the sample, with one or more probes; and (d) performing a detection step, comprising detecting the presence or absence of the amplification product, wherein the presence of the amplification product is indicative of the presence of the one or more target nucleic acids of EBV in the sample, and wherein the absence of the amplification product is indicative of the absence of the one or more target nucleic acids of EBV in the sample; and wherein the one or more set of primers and the one or more probes comprise:

(i) a set of primers comprising a first primer consisting of a nucleic acid sequence of SEQ ID NO: 1, or a complement thereof, and a second primer consisting of a nucleic acid sequence of SEQ ID NO:3, or a complement thereof, and a probe consisting of a nucleic acid sequence of SEQ ID NO:2, or a complement thereof; and/or (ii) a set of primers comprising a first primer consisting of a nucleic acid sequence of SEQ ID NO:4, or a complement thereof, and a second primer consisting of a nucleic acid sequence of SEQ ID NO:6, or a complement thereof, and a probe consisting of a nucleic acid sequence of SEQ ID NO:3, or a complement thereof.

2. The method of claim 1, wherein the sample is a biological sample.

3. The method of claim 2, wherein the biological sample is plasma or blood.

4. The method of claim 3, wherein the biological sample is plasma.

5. The method of claim 3, wherein the biological sample is blood.

6. The method of claim 1, wherein the method is for detecting a first target nucleic acid of EBV and a second target nucleic acid of EBV in a sample, wherein the one or more set of primers and the one or more probes for detecting the first target nucleic acids of EBV comprises: (i) a set of primers comprising a first primer consisting of a nucleic acid sequence of SEQ ID NO:1, or a complement thereof, and a second primer consisting of a nucleic acid sequence of SEQ ID NO:3, or a complement thereof, and a probe consisting of a nucleic acid sequence of SEQ ID NO:2, or a complement thereof; and wherein the one or more set of primers and the one or more probes for detecting the second target nucleic acids of EBV comprises: (ii) a set of primers comprising a first primer consisting of a nucleic acid sequence of SEQ ID NO:4, or a complement thereof, and a second primer consisting of a nucleic acid sequence of SEQ ID NO:6, or a complement thereof, and a probe consisting of a nucleic acid sequence of SEQ ID NO:3, or a complement thereof.

7. The method of claim 6, wherein the first target nucleic acid of EBV and the second target nucleic acid of EBV are different.

8. The method of claim 6, wherein the first target nucleic acid of EBV and the second target nucleic acid of EBV are not overlapping.

9. A method for detecting a first target nucleic acid of EBV and a second target nucleic acid of EBV in a sample, wherein the method comprises:

(a) providing a sample;

(b) performing an amplification step comprising contacting the sample with at least two sets of primers to produce an amplification product, if the first and/or second target nucleic acids of EBV are present in the sample;

(c) performing a hybridization step, comprising contacting the amplification product, if the first and/or second target nucleic acids of EBV are present in the sample, with at least two probes; and (d) performing a detection step, comprising detecting the presence or absence of the amplification product, wherein the presence of the amplification product is indicative of the presence of the first and/or second target nucleic acids of EBV in the sample, and wherein the absence of the amplification product is indicative of the absence of the first and/or second target nucleic acids of EBV in the sample; and wherein one of the at least two sets of primers and one of the at least two probes for detecting the first target nucleic acid of EBV comprises:

(i) a set of primers comprising a first primer consisting of a nucleic acid sequence of SEQ ID NO:1, or a complement thereof, and a second primer consisting of a nucleic acid sequence of SEQ ID NO:3, or a complement thereof, and a probe consisting of a nucleic acid sequence of SEQ ID NO:2, or a complement thereof; and wherein one of the at least two sets of primers and one of the at least two probes for detecting the second target nucleic acid of EBV comprises:

(ii) a set of primers comprising a first primer consisting of a nucleic acid sequence of SEQ ID NO:4, or a complement thereof, and a second primer consisting of a nucleic acid sequence of SEQ ID NO:6, or a complement thereof, and a probe consisting of a nucleic acid sequence of SEQ ID NO:3, or a complement thereof.

10. The method of claim 9, wherein the first target nucleic acid of EBV and the second target nucleic acid of EBV are different.

11. The method of claim 9, wherein the first target nucleic acid of EBV and the second target nucleic acid of EBV are not overlapping.

12. The method of claim 9, wherein the sample is a biological sample.

13. The method of claim 12, wherein the biological sample is plasma or blood.

14. The method of claim 13, wherein the biological sample is plasma.

15. The method of claim 13, wherein the biological sample is blood.

\* \* \* \* \*